(12) United States Patent
Pacetti (10) Patent No.: US 8,632,847 B2
(45) Date of Patent: Jan. 21, 2014

(54) METHODS OF MANUFACTURE OF BIORESORBABLE AND DURABLE STENTS WITH GROOVED LUMENAL SURFACES FOR ENHANCED RE-ENDOTHELIALIZATION

(75) Inventor: Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 238 days.

(21) Appl. No.: 13/182,155

(22) Filed: Jul. 13, 2011

(65) Prior Publication Data

US 2013/0017312 A1 Jan. 17, 2013

(51) Int. Cl.
*A61L 33/00* (2006.01)

(52) U.S. Cl.
USPC ......... 427/2.25; 427/2.3; 427/2.28; 427/2.24; 623/1.15; 623/1.13; 623/1.42; 623/1.11; 29/447; 29/458; 29/515; 29/516

(58) Field of Classification Search
USPC .............. 623/1.11, 1.15, 1.13, 1.42; 128/898; 29/447; 427/2.25, 2.3, 2.24, 2.28
See application file for complete search history.

(56) References Cited

U.S. PATENT DOCUMENTS

| 4,059,147 | A | | 11/1977 | Thorne | |
|---|---|---|---|---|---|
| 5,897,911 | A | * | 4/1999 | Loeffler | 427/2.25 |
| 7,673,379 | B1 | * | 3/2010 | Pacetti | 29/447 |
| 2002/0035395 | A1 | * | 3/2002 | Sugimoto | 623/1.15 |
| 2002/0147490 | A1 | * | 10/2002 | Pletzer et al. | 623/1.11 |
| 2006/0136041 | A1 | | 6/2006 | Schmid et al. | |
| 2007/0283552 | A1 | | 12/2007 | Gale et al. | |
| 2007/0293927 | A1 | * | 12/2007 | Frank et al. | 623/1.11 |
| 2009/0157158 | A1 | | 6/2009 | Ondracek et al. | |
| 2009/0292347 | A1 | * | 11/2009 | Asmus et al. | 623/1.11 |
| 2010/0244304 | A1 | | 9/2010 | Wang | |

FOREIGN PATENT DOCUMENTS

| EP | 1 769 775 | 4/2007 |
|---|---|---|
| WO | WO 01/89420 | 11/2001 |
| WO | WO 2011/044459 | 4/2011 |

OTHER PUBLICATIONS

U.S. Appl. No. 12/797,950, filed Jun. 10, 2010, Harrington et al.
Garg et al., "Coronary Stents" J. of Amer. Coll. of Cardiol. vol. 56, No. 10, pp. S1-S42 (2010).
Haudenschild et al., "Endothelial Regeneration II. Restitution of Endothelial Continuity", Lab Invest. vol. 41, No. 5, pp. 407-418 (1979).
Choubey et al. "Human aortic endothelial cell response to 316L stainless steel material microstructure", J. Mater. Sci: Mater Med. 20, pp. 2105-2116 (2009).
Palrnaz et al., "Influence of Surface Topography on Endothelialization of Intravascular Metallic Material", SCVIR vol. 10, pp. 439-444 (1999).
International Search Report and Written Opinion for PCT/US2012/044260, mailed Feb. 28, 2013, 17 pgs.

\* cited by examiner

*Primary Examiner* — Dah-Wei Yuan
*Assistant Examiner* — Andrew Bowman
(74) *Attorney, Agent, or Firm* — Squire Sanders (US) LLP (57) ABSTRACT

Methods of making bioabsorbable stents with grooved lumenal surfaces for enhanced re-endothelialization are disclosed. Methods include molding grooves on the lumenal surface of coated bioresorbable and durable stents. Methods further include molding grooves on lumenal surfaces of a bioresorbable tube and forming a scaffold from the tube.

14 Claims, 7 Drawing Sheets

METHODS OF MANUFACTURE OF BIORESORBABLE AND DURABLE STENTS WITH GROOVED LUMENAL SURFACES FOR ENHANCED RE-ENDOTHELIALIZATION

BACKGROUND OF THE INVENTION

1. Field of the Invention

This invention relates to methods of manufacturing medical devices, in particular, stents.

2. Description of the State of the Art

This invention relates to manufacturing of implantable medical devices. These devices include, but are not limited to, radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty.

Stents are used not only for mechanical intervention but also as vehicles for providing biological therapy. Medicated stents provide biological therapy through local administration of a therapeutic substance. A medicated stent may be fabricated by coating the surface of either a metallic or polymeric scaffolding with a polymeric carrier that includes an active or bioactive agent or drug. A polymeric scaffolding may also serve as a carrier of an active agent or drug.

These drug eluting stents (DES) are used in order to revascularize occluded regions of the coronary vasculature. Current DES work well yielding single digits of major adverse cardiac events (MACE) and restenosis at one year for a majority of patients. Ongoing issues are restenosis, an iatrogenic disease caused by the intervention itself, and thrombosis. While the onset of restenosis is gradual, stent thrombosis can occur suddenly and the outcome is completely contrary to the intent of revascularization. Stent thrombosis can occur at any time. However, thrombosis which occurs in the first 30 days (subacute) is thought to be due more to procedural issues, blood hypercoaguability, poor stent placement and apposition, and perhaps drug effects. At longer time points, the goal is for the vessel to heal and re-endothelialize to avoid late stent thrombosis occurring beyond 30 days. The ongoing rates of late stent thrombosis have been measured as 0.36 to 0.6% out to five years. Garg S, Serruys P. Coronary Stents. J Amer Coll Cardiol 2010; 56(10): Suppl S. S1.

The only truly non-thrombogenic surface is healthy endothelium. Consequently, rapid and complete re-endotheliazation has always been a goal for metallic, drug eluting, and bioresorbable stents in order to reduce and eliminate late stent thrombosis. As all of the drugs presently used in DES inhibit the proliferation of endothelial cells, the interest in promoting endothelial cell growth remains high. After stenting, re-endotheliatization is achieved primarily by migration of endothelial cells from adjacent arterial areas of intact endothelium. Haudenschild C C, Schutz S M. Lab Invest 1979; 41:407-418; Rogers C, Tseng D Y, et al. Circ Res 1999; 84:378-383. Based on this mechanism, extensive work has been done to understand factors which affect endothelial cell migration. For DES, a major emphasis has been on how to achieve faster, or more complete, endothelial cell migration onto stent struts.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Various embodiments of the present invention include a method of making a stent comprising: providing a stent including a bioresorbable polymer scaffold and a bioresorbable polymer coating over at least a portion of the scaffold; disposing the stent over a tubular mandrel such that a lumenal surface of the stent faces a surface of the mandrel, wherein the surface of the mandrel has a plurality of grooves aligned longitudinally; and radially compressing the stent over the surface of the mandrel such that the grooves at the surface of the mandrel form grooves on the lumenal surface of the stent, wherein the grooves on the luminal surface are aligned along a cylindrical axis of the stent.

Further embodiments of the present include a method of making a stent comprising: providing a bioresorbable polymer tube having an original diameter; disposing the tube over a tubular mandrel such that a lumenal surface of the tube faces a surface of the mandrel, wherein the surface of the mandrel has a plurality of grooves aligned longitudinally; radially compressing the tube over the surface of the mandrel such that the grooves at the surface of the mandrel form grooves on the lumenal surface of the tube; and forming a stent scaffold from the tube after forming the grooves, wherein the lumenal surface of the stent scaffold includes grooves formed from the radial compression that are aligned along a cylindrical axis of the stent scaffold.

Additional embodiments of the present invention include a method of making a stent comprising: conveying a melted polymer from an extruder barrel through an annulus of an annular die to form a tube, wherein the annular die has a first surface which forms an outer surface of the tube and an second surface that forms an inner surface of the tube, wherein the second surface of the annular die has grooves aligned longitudinally; allowing the grooves on the second surface of the annular die to form grooves in the inner surface of the tube formed as the polymer passes through the annular die; radially expanding the tube to an expanded diameter, wherein the radial expansion modifies a size of the grooves;

and fabricating a stent scaffold from the tube with the expanded diameter, wherein a lumenal surface of the stent scaffold has the modified grooves that are aligned longitudinally.

Other embodiments of the present invention include a method of making a stent comprising: providing a stent having a metallic scaffold and a polymer coating over the scaffold; disposing the stent over a tubular mandrel such that a lumenal surface of the stent faces a surface of the mandrel, wherein the surface of the mandrel has a plurality of grooves aligned longitudinally; and radially compressing the stent over the surface of the mandrel such that the grooves at the surface of the mandrel form grooves on the coating over the lumenal surface of the stent.

Further embodiments of the present invention include a method of making a stent comprising: providing a stent having a metallic scaffold; disposing the stent over a tubular mandrel such that a lumenal surface of the scaffold faces a surface of the mandrel, wherein the surface of the mandrel has a plurality of grooves aligned longitudinally; and radially compressing the stent over the surface of the mandrel such that the grooves at the surface of the mandrel form grooves on the lumenal surface of the metal of the scaffold.

DETAILED DESCRIPTION OF THE INVENTION

One example of early work directed to promoting endothelialization was measurement of adhesion of endothelial cells on 316L stainless steel surfaces with different etched grain sizes. Choubey A, Marton 0, Sprague E A. J Mater Sci: Mater Med 2009; 20:2105-2116. This work demonstrated that endothelial cells attached better to the 16 micron grain size. That 16 micron periodicity was advantageous, at least in cell culture. In another study, the effect of grooves in a metal surface was examined on endothelial cell migration rates in vitro. Palmaz J C, Benson A, Sprague E A. JVIR 1999; 10:439-444. Grooves of various sizes were made in nitinol with a silicon carbide-impregnated cloth. The migration distances of human aortic endothelial cells on the various surfaces shows faster endothelial cell migration on unidirectional grooves of a certain size (15-22 microns). The cells aligned with the grooves, elongated, and became more numerous on grooved surfaces. More recent endothelial migration data in vitro showed similar results. Sprague E A, Impact of Texture and Strut Thickness: experimental and clinical evidence, TCT 2010, Washington. While these in vitro results are intriguing, a reasonable question is whether they can be repeated in vivo. Sprague also presented in vivo endothelialization data which was gathered in a porcine carotid model using a stent which superficially resembles the Palmaz-Schatz. Groove size was 12-15 microns. A large, and statistically significant difference in endothelial coverage was seen at 7 days, while at 3 weeks and beyond there was no difference as the vessels were fully endothelialized by then.

With results such as this, it is an open question why no manufacturer has conducted clinical investigations into the utility of a lumenally grooved stent. There are several reasons why this concept has not made its way into a product. First, there are still questions as to how to mass produce stents with grooves. Second, there have been other, more attractive technologies to pursue for stents such as drug delivery and better acute performance. Third, determining benefit in a human clinical trial setting would be expected to be challenging. For a DES, it would not be expected that grooves would improve antirestenotic efficacy. It is hypothesized that grooves would improve re-endothelialization which occurs at 3-6 months in humans. However, there is no current method to directly assess re-endothelialization in humans unless they expire during the trial. Other clinical endpoints which may be affected by re-endothelialization such as MACE, target vessel failure (TVF), myocardial infarction (MI), death, and stent thrombosis can be monitored, but are currently at low incidence rates. It is statistically challenging to show improvement in these endpoints with current generation DES and financially driven pessimism usually wins out in deciding not to fund product development or a trial. Still, as DES and BMS continue to evolve and mature there is a need to improve these devices further, even if by only an incremental amount. Therefore, constructs and production techniques are needed to apply the grooved surface concept to bioresorbable and to polymer coated metallic DES.

The methods described herein are generally applicable to a variety of implantable medical device. In particular, the methods can be applied to tubular implantable medical devices such as self-expandable stents, balloon-expandable stents, and stent-grafts.

Figure 1:
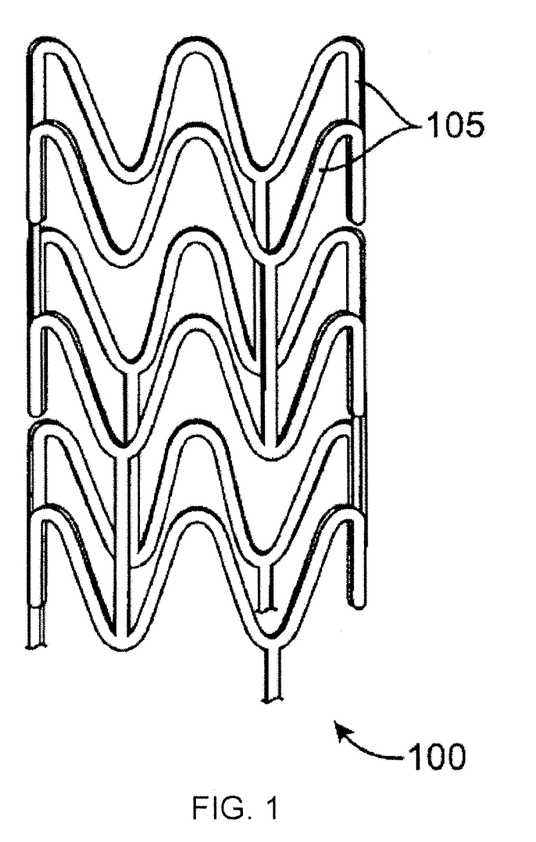
FIG. 1 depicts a stent.

A stent may include a pattern or network of interconnecting structural elements or struts. FIG. 1 depicts a view of a stent

100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited.

A stent such as stent 100 may be fabricated from a tube or a sheet by rolling and bonding the sheet to form the tube. A polymer tube or sheet can be formed by extrusion or injection molding while a metallic tube can be made by extrusion or molten metal casting. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device of the present invention can be made partially or completely from a biodegradable, bioresorbable, bioabsorbable, or biostable polymer. A polymer for use in fabricating an implantable medical device can be biostable, bioresorbable, bioabsorbable, biodegradable or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

A stent made from a bioresorbable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

A bioresorbable scaffolding can be made partially or completely of polymers including poly(L-Lactide) (PLLA), poly (L-lactide-co-D,L-lactide) (PLDLA), poly(D-lactide) (PDLA), poly(D,L-lactide) (PDLLA), polyglycolide (PGA), poly(D,L-lactide-co-glycolide) (PLGA), and poly(L-lactide-co-glycolide) (PLLGA). PLLA is a suitable polymer for a stent scaffold due to its high crystallinity and mechanical strength. Greater flexibility for a bioresorbable scaffold can be achieved by use of PLDLA. With respect to PLGA, the stent scaffolding can be made from PLLGA with a mole % of GA between 5-15 mol %. The PLGA can have a mole % of (LA:GA) of 85:15 (or a range of 82:18 to 88:12), 95:5 (or a range of 93:7 to 97:3), or commercially available PLGA products identified as being 85:15 or 95:5 PLGA. Such polymers may also be used for a bioresorbable coating on a bioresorbable scaffolding. The coating polymer may be combined with a drug, such as an antiproliferative or anti-inflammatory agent.

Detailed discussion of the manufacturing process of a bioresorbable stent can be found elsewhere, e.g., US 2007/0283552. The fabrication methods of a bioresorbable stent can include the following steps:

(1) forming a polymeric tube from a bioresorbable polymer resin using extrusion, (2) radially expanding the formed tube to increase radial strength, (3) forming a stent scaffolding from the expanded tube by laser machining a stent pattern in the expanded tube with laser cutting (in exemplary embodiments, the strut thickness can be 100-200 microns, or more narrowly, 120-180, 130-170, or 140-160 microns), (4) forming a therapeutic coating over the scaffolding, (5) crimping the stent over a delivery balloon to a reduced diameter for delivery, and (6) sterilization with election-beam (E-beam) radiation.

With respect to step (1), an extruder generally includes a barrel through which a polymer melt is conveyed from an entrance to an exit port. A polymer resin is fed to the extruder barrel near its proximal end from a hopper as a solid, for example, in the form of a pellet. The polymer in the extruder barrel is heated to temperatures above the melting temperature (Tm) of the polymer and exposed to pressures that are generally far above ambient.

In the radial expansion step (2), the extruded polymer tube may be expanded by blow molding. The tube is disposed in a mold. The tube is expanded by increasing the pressure inside the mold and heating the tube. The tube expands against the inner surface of the mold so that the outer diameter of the expanded tube is at the inner diameter of the tube. The tube may be heated to temperature above the glass transition temperature (Tg) of the tubing polymer. For example, PLLA has Tg of about 60 to 65 deg C. (Medical Plastics and Biomaterials Magazine, March 1998), so the expansion temperature may be 60 to 80 deg C. The percent radial expansion (% RE) is defined as 100%×(Inside Diameter of Expanded Tube/Original Inside Diameter of Tube−1). The % RE can be 100 to 200, 200 to 300, 300 to 400, or more than 400. The tube may also be axially deformed during the radial expansion step.

In the coating step (4), a coating material is applied to the surface of the scaffolding to form the coating. The coating material is a solution including dissolved polymer (e.g., PDLLA) mixed with a drug (e.g., everolimus). After application of the coating material, the solvent is removed, leaving a coating of polymer and drug. A coating of a desired thickness may be formed by multiple coating material applications. In between coating applications, solvent is removed or partially removed, followed by application of additional coating material.

Certain embodiments of the present invention include methods of making a bioabsorbable stent having a lumenal surface that has grooves aligned longitudinally or parallel with the cylindrical axis of the stent. The grooves promote re-endothelialization on the lumenal surface when the stent is implanted. The stent may include a bioresorbable stent scaffolding structure made of a polymer and a coating over the scaffolding that is made of a different polymer and a drug. In some embodiments, the luminal surface is free of coating and the grooves are in the polymer of the scaffold on the luminal surface. Such a scaffold can further include a coating on the abluminal surface of the scaffold.

An exemplary bioresorbable stent can include a PLLA scaffolding with coating including PDLLA. The coating can further include an antiproliferative drug such as everolimus. The thickness of the coating can be 1 to 3 microns.

Further embodiments of the invention include methods of making a stent including a metallic stent scaffold with a polymer coating on at least the lumenal surface of the stent scaffold with grooves in the lumenal surface extending longitudinally or parallel with the cylindrical axis of the stent. Other embodiments include a metallic scaffolding with grooves in the metallic luminal surface which is free of a coating and optionally, a coating on the abluminal surface. An exemplary stent can include a metallic scaffolding with a poly(vinylidene fluoride-co-hexafluoropropylene) (PVDF-HFP) coating that is mixed with everolimus.

Figure 2:
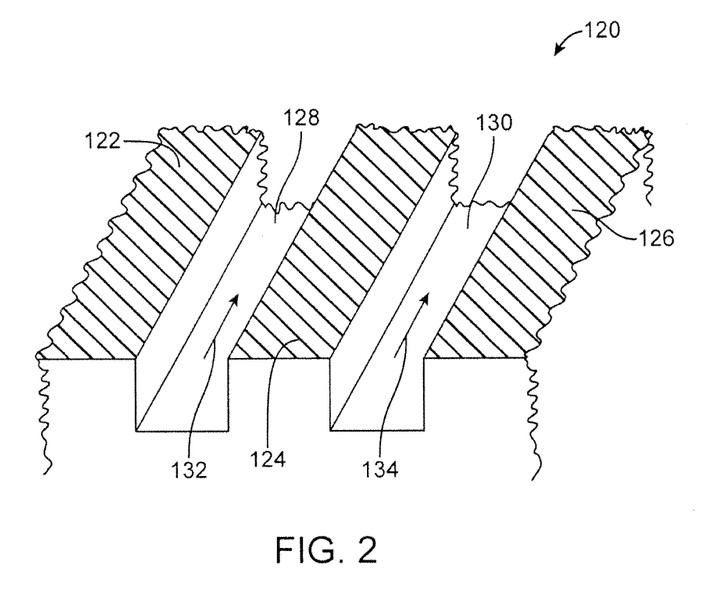
FIG. 2 depicts a portion of a grooved surface to illustrate its features.
Figure 3A:
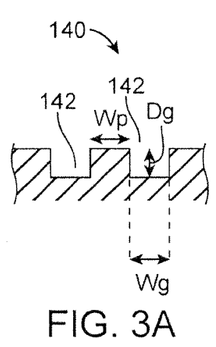
FIG. 3A depicts a grooved surface with rectangular grooves.
Figure 3B:
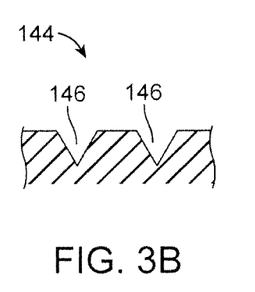
FIG. 3B depicts a grooved surface with triangular grooves.
Figure 3C:
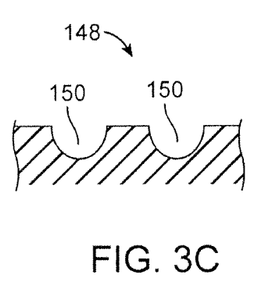
FIG. 3C depicts a grooved surface with semicircular grooves.

A groove may be defined as a long narrow furrow, channel, or recess in a surface. FIG. 2 depicts a portion 120 of a grooved surface. Portion 120 includes plateau surfaces 122, 124, and 126, which are raised surfaces between grooves, and grooves 128 and 130. Grooves 128 and 130 run along an axis or direction as shown by arrows 132 and 134, respectively. A cross-section of the grooves transverse to the axis of a groove can be rectangular, sinusoidal, semicircular, triangular, or any other regular or irregular shape. Exemplary cross-sections are shown in FIG. 3A-C. FIG. 3A depicts a grooved surface 140 with rectangular grooves 142. FIG. 3B depicts a grooved surface 144 with triangular grooves 146. FIG. 3C depicts a grooved surface 148 with semicircular grooves 150.

The grooves may be characterized by depth of the grooves (Dg) and width of the grooves (Wg) (or periodicity) and the width of plateau (Wp), as shown in FIG. 3A. Dg may correspond to the deepest point of the groove. Wg may correspond to the widest point of the groove. $W_P$ may be 2 to 40 microns, or more narrowly 10 to 20 microns. Wg may be 5 to 30 microns, or more narrowly, 10 to 20 microns. Dg may be 0.5 to 20 microns or more narrowly, 1 to 10 microns.

In some embodiments of a bioabsorbable scaffold with or without a coating, part or the entire lumenal surface of the scaffold has grooves. The grooves may be aligned with the longitudinal axis of the scaffold. However, in these and other embodiments of the present invention, the grooves may be aligned along any direction, for example, transverse to the cylindrical axis, between 0 and 90 degrees to the cylindrical axis, which includes spiral or helical grooves. Longitudinally aligned grooves are preferred since they appear to be most favorable for promoting re-endothelialization.

Figure 4:
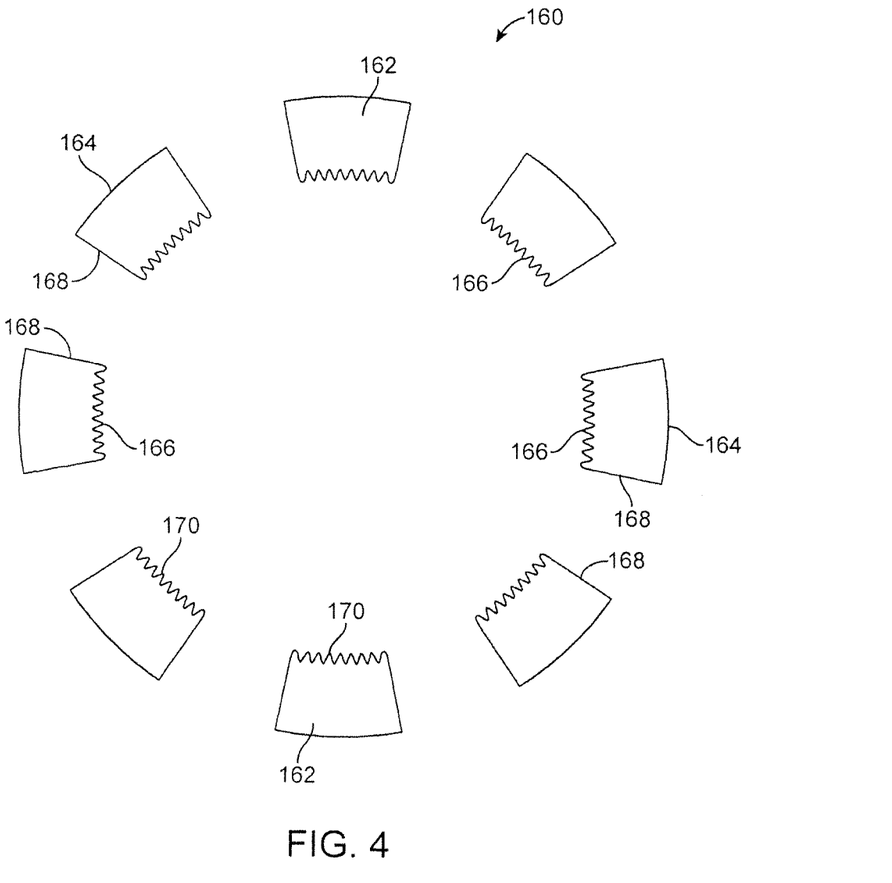
FIG. 4 depicts a radial cross-section of a scaffold 160 with grooves in the lumenal surface.

FIG. 4 depicts a radial cross-section of a scaffold 160 with grooves in the lumenal surface. Strut cross-sections 162 have an abluminal surface 164, a lumenal surface 166, and side wall surfaces 168. Grooves 170 are shown in lumenal surfaces 166 with the size of the grooves exaggerated for clarity. Additionally, the coating is not shown for clarity.

In certain embodiments, grooves may be formed in a lumenal surface of a stent that includes a bioresorbable polymer scaffold and a bioresorbable polymer coating on or above at least the lumenal surface of the scaffold. In another embodiment, grooves may be formed in the luminal surface of a stent that includes a bioresorbabale polymer scaffold with no coating on the luminal surface of the coating and optionally a bioresorbable polymer coating on at least the abluminal surface. Embodiments of methods include molding grooves in the luminal surface of the stent. These embodiments include disposing the stent over a tubular mandrel having a plurality of longitudinal grooves in the surface of the mandrel. For coronary applications, the inner diameter of the scaffold can be 3 to 4 mm, or more narrowly, 3 to 3.5 mm. For peripheral applications the diameter of the scaffold can be 4 to 6 mm, or more narrowly, 5 to 6 mm, or greater than 6 mm.

The inner diameter of the scaffolding may initially be greater than diameter of the mandrel, for example, 0 to 1% greater, 1-5% greater, 5-10% greater, or more than 10% greater. Alternatively, the diameter of the scaffold may be the same as the diameter of the mandrel, and thus, initially has a tight fit over the mandrel. The lumenal surface of the stent faces a surface of the mandrel. The stent may then be radially compressed over the surface of the mandrel such that the grooves at the surface of the mandrel form or mold grooves on the coating of the lumenal surface of the scaffold or on the scaffold. The formation and retention of the grooves may be facilitated by softening the lumenal surface of the scaffold.

In some embodiments, the stent may be radially compressed by disposing the stent and the mandrel within a crimping device adapted to apply radial pressure to a stent. The radial pressure may reduce its diameter. In this, and in other embodiments, unless otherwise noted, the pressure applied to the stent to form the grooves may be between 10 and 500 psi. An exemplary crimping device is a sliding wedge or iris crimper in which adjacent pie-piece-shaped sections or wedges move inward and twist, much like the leaves in a camera aperture. Other types of crimping devices that may be used are described in US 2005/0119720.

Figure 5:
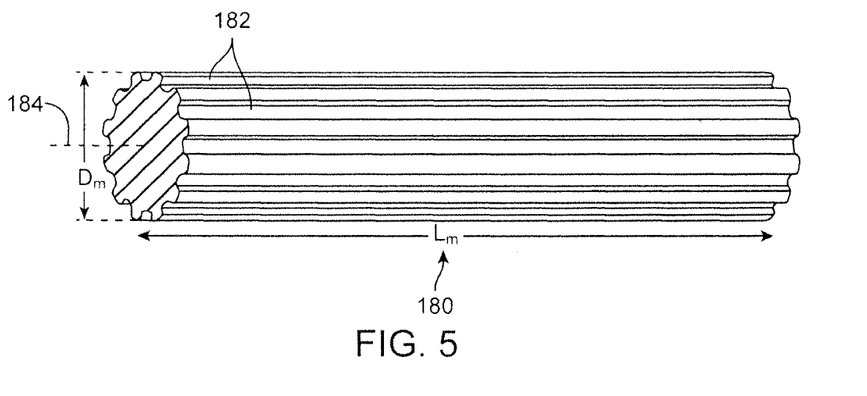
FIG. 5 depicts a schematic illustration of a mandrel with grooves in its surface aligned longitudinally or parallel along its cylindrical axis.

FIG. 5 depicts a schematic illustration of a mandrel 180 with grooves 182 in its surface aligned longitudinally or parallel to its cylindrical axis 184. Mandrel 180 has a diameter Dm and a length Lm. The size of the grooves is exaggerated for clarity.

The mandrel can be hollow or solid. The mandrel can be made of a metal or ceramic material. Exemplary metallic materials include 300 series stainless steels, 316L stainless steel, tool steels, chrome molybdenum steels, cobalt chromium based alloys such as L-605, cobalt based satellite alloys, cobalt nickel alloys such MP35N, and nickel-based alloys. The grooves in the surface of the mandrel may be formed using a variety of techniques including electrical discharge machining, laser machining, and ion beam milling.

Figure 6A:
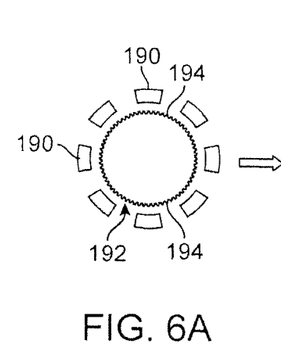
FIG. 6A depicts a radial cross-section of struts of a stent disposed over a mandrel with grooves on its surface that are aligned longitudinally.
Figure 6B:
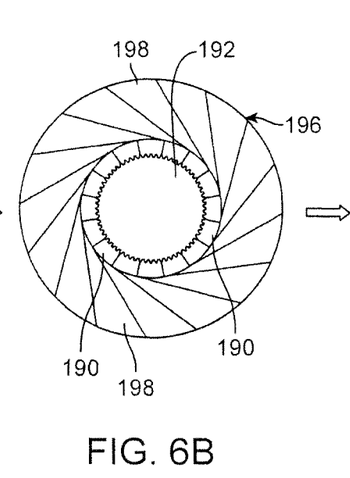
FIG. 6B depicts the stent and mandrel of FIG. 6A disposed within the aperture of a sliding wedge crimper.
Figure 6C:
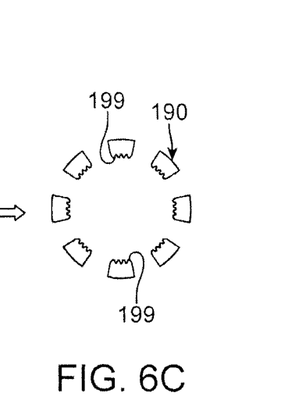
FIG. 6C illustrates the stent of FIG. 6B as shown by struts after the crimping procedure showing the grooves formed in the lumenal surface.

FIGS. 6A-6C illustrate a process of forming grooves in a lumenal surface of a bioabsorbable stent. FIG. 6A depicts a radial cross-section of struts 190 of a stent disposed over a mandrel 192 with grooves 194 on its surface that are aligned longitudinally. FIG. 6B depicts the stent and mandrel disposed within the aperture of a sliding wedge crimper 196 which includes a plurality of sliding wedges 198 that form the aperture. Sliding wedges 198 slide and rotate inward, decreasing the size of the aperture. As the aperture size decreases, the surface of the wedges at the aperture apply a radial pressure on struts 190. Struts 190 are pressed into the grooved surface of mandrel 192 which forms or molds grooves in the lumenal surface of the stent.

The aperture is of the crimper is then retracted and the stent and mandrel are removed from the crimper. The diameter of the stent may then increase back to or close to its original diameter. FIG. 6C illustrates the stent as shown by struts 190 after the crimping procedure showing the grooves in the lumenal surface 199 that are formed.

When forming grooves in a coated luminal surface, since both the scaffold and coating are polymer, the grooves may be formed in the coating polymer and the scaffold polymer. Therefore, the grooves can have a depth greater depth than the thickness of the coating. As discussed, the luminal surface of the scaffold may also be free of coating polymer in which case the grooves are formed only in the scaffold polymer.

As indicated, the formation of the grooves may be facilitated by softening the polymer at the lumenal surface or surface region. In some embodiments, the lumenal surface of the stent may be heated to soften the polymer at the lumenal surface. In such embodiments, the polymer surface may be heated by the mandrel. The mandrel or the surface of the mandrel may be heated in a number ways. The mandrel may be heated by an electrical heating element or elements disposed within the mandrel. Additionally, infra-red or microwave elements within the mandrel can heat the mandrel. In other embodiments, the mandrel can be heated by using a hollow mandrel and blowing a warm gas through the mandrel.

In some embodiments, the temperature of the mandrel surface or the polymer surface during the radial compression may be above ambient temperature to Tg of the polymer at the lumenal surface. For example, between 30 degrees C. to Tg.

In other embodiments, the temperature during radial compression is above the Tg of the polymer at the lumenal surface. For example, the temperature is Tg to Tg+10 deg C., Tg+10 deg C. to Tg+20 deg C., or greater than Tg+20 deg C. For example, Tg of PDLLA is 55 to 60 deg C. Medical Plastics and Biomaterials Magazine, March 1998.

The temperature for heating a stent with a PDLLA coating over a PLLA scaffold may be 55 to 70 deg C., or more narrowly, 55 to 60 deg C. In other embodiments, the temperature of the mandrel or the polymer surface can be 30 to 40 deg C., 40 to 50 deg C., 50 to 60 deg C., 60 to 70 deg C., 70 to 80 deg C., or greater than 80 deg C. The temperature should be below a temperature or temperature range at which a drug in the coating becomes unstable or is subject to decomposition. Typical minimum stability temperatures for drugs may be in the range of 60 to 100 deg C. For example, everolimus is stable up to 60 deg C. and stable for short periods up to 80 deg C., and unstable above 80 deg C.

In some embodiments, the polymer at the lumenal surface of the stent may be softened by a solvent that swells or is capable of dissolving the polymer at the lumenal surface. In such embodiments, the solvent may be applied to the lumenal surface, for example, by spraying, dipping, brushing, or some other way. After application of the solvent to the lumenal surface, the stent may then be radially compressed over the mandrel to form grooves in the softened polymer surface. The solvent may then be removed from the stent by a drying step, for example, by blowing a warm gas on the lumenal surface or baking in a vacuum or convection oven.

As used herein, a "solvent" for a given polymer can be defined as a substance capable of swelling the polymer or dissolving or dispersing the polymer to form a uniformly dispersed mixture at the molecular- or ionic-size level. Swelling of a polymer occurs when a solvent in contact with a sample of the polymer diffuses into the polymer. L. H. Sperling, Physical Polymer Science, $3^{rd}$ ed., Wiley (2001). Thus, a swollen polymer sample includes solvent molecules dispersed within the bulk of the polymer. Dissolution of the polymer occurs when polymer molecules diffuse out of the swollen polymer into solution.

In other embodiments of softening with a solvent, the solvent may be applied to the surface of the mandrel prior to radially compressing the stent over the grooved mandrel surface. As the stent is radially compressed over the mandrel, the solvent on the mandrel softens the polymer at the lumenal surface of the stent.

Representative examples of solvents that may be used in accordance with the present invention include, but are not limited to, acetone, 2-butanone, chloroform, hexafluoroisopropanol, trifluoroethanol, 1,4-dioxane, tetrahydrofuran (THF), dichloromethane, tetrachloroethylene, acetonitrile, dimethyl sulfoxide (DMSO), and dimethylformamide (DMF), cyclohexane, toluene, xylene, cyclohexanone, ethyl acetate, and methyl acetate. Representative solvents that will dissolve a PDLLA polymer at a lumenal surface include acetone, THF and chloroform. Representative solvents that will swell a PDLLA polymer at a lumenal surface include ethanol, acetonitrile, and n-butanol.

As indicated above, the coating on a scaffold is formed by applying a polymer solution to a scaffold and then removing the solvent to form the polymer coating. In some embodiments, the coating step is modified to provide a polymer coating that includes residual solvent in the coating sufficient to soften the coating. In such embodiments, the drying step during the coating process is performed so that residual solvent remains in the coating. The residual solvent content in the coating may be 1 to 10 wt %, 1 to 5 wt %, 5 to 10 wt %, or greater than 10 wt % of the total mass of the coating. After the formation of the grooves in the lumenal surface, the residual solvent can be removed in a drying step.

In further embodiments, a stent including a bioresorbable polymer scaffold with a bioabsorbable polymer coating with a grooved lumenal surface can be made by molding grooves into an inner or lumenal surface of a polymeric tube. A scaffold pattern may then be formed from the tube. The scaffold may then be coated in a manner that the lumenal surface coating includes grooves. In such embodiments, a polymeric tube may be disposed over a tubular mandrel having a plurality of longitudinal grooves in the surface of the mandrel. The diameter of the polymeric tube may the diameter at which a scaffold is formed from the tube or the target diameter of the fabricated stent. In some embodiments, the polymer tube is a radially expanded tube, as descried above in the exemplary fabrication process of a bioabsorbable stent.

The inner diameter of the tube may the same as the outer diameter of the mandrel. Alternatively, the diameter of the tube may be slightly larger than of the mandrel. For example, the tube diameter may be less 0.05 mm greater, 0.5 to 0.1 mm greater, 0.1 to 0.3 mm greater, or more than 0.3 mm greater than the inner diameter of the mandrel. The tube may then be radially compressed over or into the surface of the mandrel such that the grooves at the surface of the mandrel form or mold grooves in the lumenal surface of the tube.

As above, the formation of the grooves may facilitated by softening the lumenal surface of the scaffold. The mandrel may be heated during the radial compression which heats the polymer at the lumenal surface of the tube. Heating with a mandrel is described above for heating the lumenal surface of a stent. The temperature of the mandrel or the polymer surface can be 30 to 40 deg C., 40 to 50 deg C., 50 to 60 deg C., 60 to 70 deg C., 70 to 80 deg C., or greater than 80 deg C. Since there may be no drug at the tube luminal surface, the temperature may be higher when molding grooves in the tube than for the coating.

Additionally, the polymer at the lumenal surface of the tube may be softened by a solvent that swells or is capable of dissolving the polymer at the lumenal surface. The solvent may be applied to the lumenal surface of the tube, for example, by spraying, dipping, brushing, or some other way. After application of the solvent to the lumenal surface of the tube, the tube may then be radially compressed over the mandrel to form grooves in the softened polymer surface. The solvent may then be removed from the tube by a drying step, for example, by blowing a warm gas on the lumenal surface or baking in a vacuum or convection oven.

Additionally, as discussed above, the solvent may be applied to the surface of the mandrel prior to radially compressing the stent over the grooved mandrel surface. As the stent is radially compressed over the mandrel, the solvent on the mandrel softens the polymer at the lumenal surface of the tube.

A solvent may be used that swells or dissolves the tube polymer. Representative solvents that will dissolve a PLLA polymer at a lumenal surface of a PLLA tube include chloroform, hexafluoroisopropanol, and dichloromethane. Representative solvents that will swell a PLLA polymer at a lumenal surface of a PLLA tube include acetone, THF, and toluene.

Figure 7A:
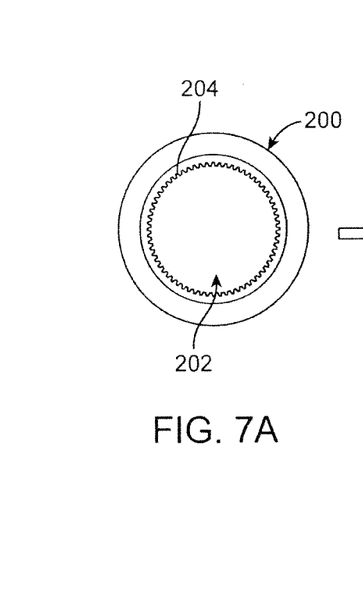
FIG. 7A depicts the radial cross-section of a polymer tube disposed over a mandrel with grooves on its surface that are aligned longitudinally.
Figure 7B:
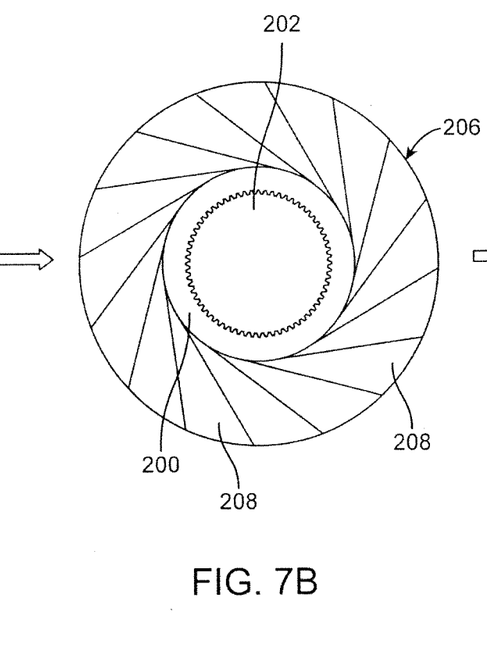
FIG. 7B illustrates the tube and mandrel of FIG. 7A disposed within the aperture of a sliding wedge crimper.
Figure 7C:
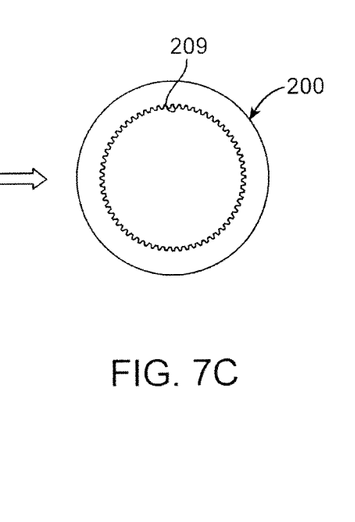
FIG. 7C illustrates the tube of FIG. 7B after the crimping procedure showing the grooves formed in the lumenal surface.

FIGS. 7A-7C illustrate the process of forming grooves in a lumenal surface of a tube. FIG. 7A depicts the radial cross-section of a polymer tube 200 disposed over a mandrel 202 with grooves 204 on its surface that are aligned longitudinally. FIG. 7B illustrates tube 200 and mandrel 202 disposed within the aperture of a sliding wedge crimper 206. Sliding wedges 208 slide inward, decreasing the size of the aperture and the surface of the sliding wedges at the aperture apply a radial pressure on tube 200. Tube 200 is pressed into the grooved surface of mandrel 202 which forms or molds grooves in the lumenal surface of tube 200.

The aperture of the crimper is then retracted and the tube and mandrel are removed from the crimper. FIG. 7C illustrates tube 200 after the crimping procedure showing the grooves in the lumenal surface 209 that are formed.

A scaffold with a stent pattern may then be formed from the tube having the lumenal surface with grooves. The scaffold may be formed using exemplary laser cutting methods described in US 2007/0283552 and U.S. patent application Ser. No. 12/797,950. The scaffold that is formed has grooves on the lumenal surface of the struts.

A therapeutic coating may then be formed on the scaffold, including on the lumenal surface with grooves. The coating may be formed on the lumenal surface in a manner that results in a lumenal surface with a coating that has grooves. The coating process is performed in a manner that prevents filling in the grooves resulting in a coating that planarizes the surface or a planarizing coating. Therefore, the coating process is performed to provide a conformal or close to a conformal coating on the surfaces inside of the grooves, rather than filling in the grooves. A conformal coating, as used herein, is a coating having a uniform thickness over a particular portion of a surface or surfaces.

Alternatively, a coating can be formed on the abluminal surface of the scaffold with no coating on the luminal surface with grooves.

Figure 8A:
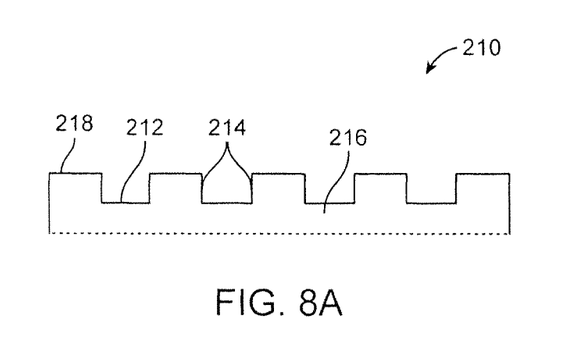
FIG. 8A depicts a cross-section of a surface section that has grooves.
Figure 8B:
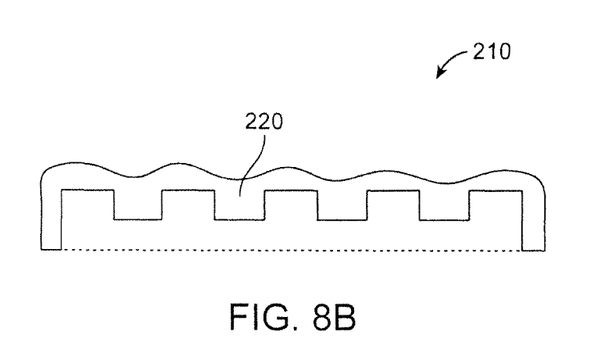
FIG. 8B depicts the surface section of FIG. 8A with a planarizing coating that fills in grooves and planarizes the surface.
Figure 8C:
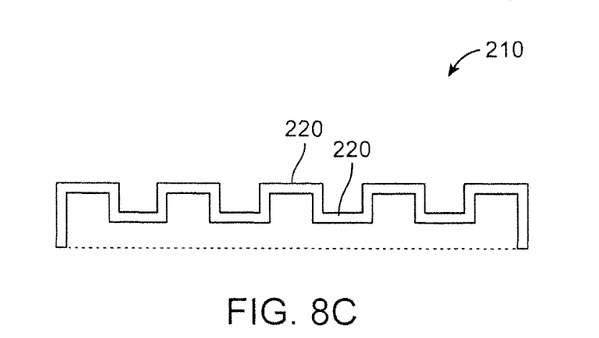
FIG. 8C depicts the surface section of FIG. 8A with a conformal coating.

FIGS. 8A-C illustrate the difference between a planarizing and conformal coating. FIG. 8A depicts a cross-section of a surface section 210 that has grooves 212. Surface section 210 include plateau surfaces 218 and grooves 212 which are defined by side wall surfaces 214 and bottom surfaces 216. FIG. 8B depicts surface section 210 with a planarizing coating that fills in grooves 212 and planarizes the surface. FIG. 8C depicts surface section 210 with a conformal coating 220. Coating 220 has a coating thickness that is uniform across plateau surfaces 218, side wall surfaces 214 and bottom surfaces 216.

The width and depth of grooves 202 are decreased by the conformal coating 220, however, conformal coating provides maximum preservation of the grooved surfaces. The planarizing coating and conformal coating are extreme cases of a coating of a grooved surface. Different degrees of nonuniformity in coating thickness in the grooves can lead to different degrees of preservation of the depth and width of the grooves.

The coating process parameters can be modified to provide a high degree of uniformity of coating thickness in the grooves resulting in a coating that is conformal or close to it. Coating parameters that favor conformal coating include the use of solvents for coating solutions that are fast evaporating and coating solutions that are relatively high viscosity. Representative solvents that are fast evaporating include acetone and dichloromethane. Increasing the percent solids of polymer in the coating will raise the coating viscosity, tending towards a more conformal coating. Applying the coating under conditions of elevated temperature, or under with rapid drying such as by directing warm air at the coating, will cause the coating to solidify more rapidly, yielding a more conformal coating.

In further embodiments, a stent with longitudinally aligned grooves in the lumenal surface can be formed from a tube having grooves formed during the extrusion process that makes the tube. In the tube extrusion process, a melted polymer is conveyed from an extruder barrel through an annulus of an annular die to form a tube. The annular die has a first surface which forms an outer surface of the tube and a second surface that forms the inner surface of the tube. Embodiments of the present invention include an annular die having an second surface that has grooves aligned in the longitudinal direction. As the polymer is conveyed through the die the grooves on the first surface of the annular die form grooves in the inner or lumenal surface of the tube.

Figure 9A:
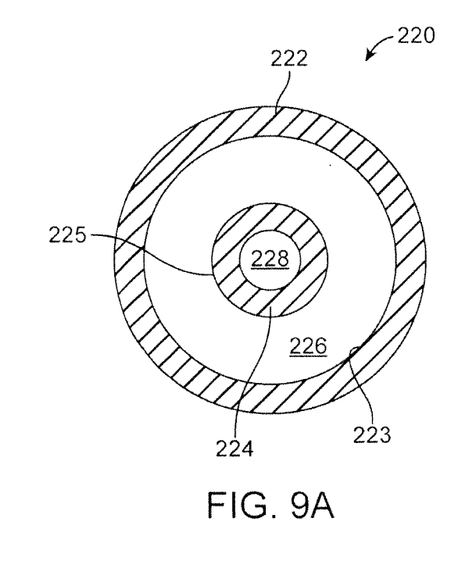
FIG. 9A shows a radial cross-section of a conventional extrusion die.

FIG. 9A shows a radial cross-section of a conventional extrusion die 220. Extrusion die 220 includes an outer hollow tubular section 222 having an inner surface 223 and an inner hollow tubular section 224 having an outer surface 225. The polymer extrudate is conveyed through annular cavity 226 between inner surface 223 and outer surface 225 to form a tube. The outer surface of the tube is formed by inner surface 223 of tubular section 222 and the inner surface of the tube is formed by outer surface 225 of inner tubular section 224. Nitrogen gas is passed through tubular cavity 228 to facilitate control of the tube dimensions.

Figure 9B:
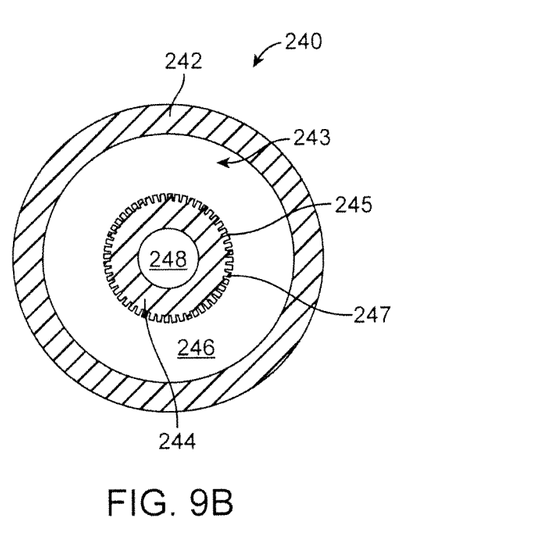
FIG. 9B shows a radial cross-section of an extrusion die of the present invention.

FIG. 9B shows a radial cross-section of an extrusion die 240 for use in the present invention. Extrusion die 240 includes an outer hollow tubular section 242 having an inner surface 243 and an inner hollow tubular section 244 having an outer surface 245. As shown in FIG. 9B, outer surface 245 has longitudinally aligned grooves 247. The polymer extrudate is conveyed through annular cavity 246 between inner surface 243 and outer surface 245 to form a tube. As the polymer extrudate is conveyed, grooves 247 on outer surface 245 form grooves in the lumenal surface of the tube.

Figure 10:
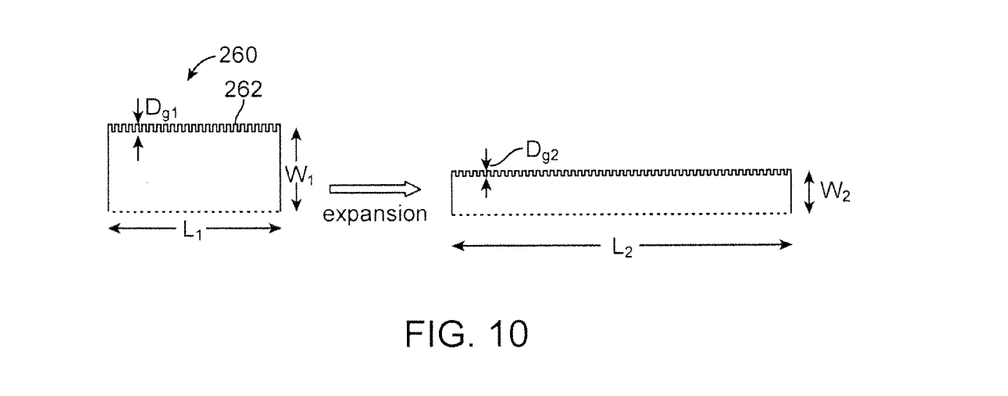
FIG. 10 depicts a section of a tube wall before and after radial expansion.

After forming the tube with lumenal grooves in the extrusion step, the tube may then be radially expanded, as described above. A scaffold may then be formed from the tube by laser machining. The radial expansion process increases the circumference and decreases the thickness of the tube. Due to deformation of the tube, the radial expansion step changes the width and depth of the grooves formed during the extrusion process. Specifically, it is expected that radial expansion increases the width and decreases the depth of the grooves. FIG. 10 depicts a section of a tube wall before and after radial expansion with the curvature omitted for the purpose of simplification. FIG. 10 depicts a section 260 of a tube wall that has an initial length L1, initial thickness W1, and initial groove depth Dg1. After expansion the section has a larger length L2, a smaller thickness W2. The final groove depth Dg2 is also smaller than the initial groove depth Dg1.

Thus, in order to obtain grooves in the scaffolding of a target width and depth, the grooves formed in the extrusion process should be narrower and deeper than the target width and depth, respectively, in a scaffolding. The groove size required at the extrusion process to obtain a target groove size in a radial expanded tube can be determined experimentally. Tubes with different groove sizes can be radially expanded and the change in groove size observed.

Further embodiments include making a stent including a metallic scaffold and a polymer coating on the scaffold with grooves in the coating on the lumenal surface stent. In some embodiments, a method includes disposing a coated metal stent over a mandrel such that a lumenal surface of the stent faces a surface of the mandrel. The surface of the mandrel has a plurality of grooves aligned longitudinally. The stent is radially compressed over the surface of the mandrel such that the grooves at the surface of the mandrel form or mold grooves on the coating over the lumenal surface of the stent.

In such embodiments, the stent can be radially compressed using a crimper, as described above. The stent and mandrel may be placed inside a sliding wedge crimper which applies pressure to the stent and compresses the lumenal surface of the stent on the surface of the mandrel and forms grooves in the coating at the lumenal surface of stent. The coating may be softened to facilitate formation of the grooves.

The coating may be softened by heating the coating during compression through the use of a heated mandrel, which is described above. The temperature of the mandrel or the polymer surface can be less than 50 deg C., less than 60 deg C., less than 80 deg C., 30 to 40 deg C., 40 to 50 deg C., 50 to 60 deg C., 60 to 70 deg C., 70 to 80 deg C., or greater than 80 deg C. The temperature should below a temperature that may cause damage to a drug that is within the coating. A minimum decomposition temperature for drugs, generally, may be in the range of 80 to 100 deg C.

A coating on a metallic scaffold can include more than one layer. The layers can be made of different polymers. Also, one layer may include a drug, while another layer may be free of drug, except for incidental diffusion of drug from a drug containing layer to an adjacent layer. Exemplary coatings can include a primer layer that is directly in contact with the metal scaffolding. The primer layer may be made of a polymer that has good adhesion to the metal and may be free of drug. A drug layer may be disposed on the primer layer. The drug layer may be made of a mixture of a polymer and a drug. The polymer may be selected due to desirable release properties for the drug.

The total thickness of the coating may be 2 to 20 microns, or more narrowly, 2 to 10 microns, 3 to 10 microns, 3 to 8 microns, or 3 to 5 microns. The thickness of a primer layer may be 1 to 15 microns, or more narrowly, 1 to 10 microns, or 1 to 5 microns. The thickness of a therapeutic layer may be 2 to 15 microns, or more narrowly, 2 to 10 microns, or 2 to 5 microns.

An exemplary primer layer is poly(n-butyl methacrylate) (PBMA). A therapeutic layer that contains polymer and a drug may be on the primer layer. An exemplary polymer for a drug layer may be poly(vinylidene fluoride-co-hexafluoropropylene) (PVDF-HFP) and an exemplary drug is everolimus. PVDF-HFP melts at about 130-160 deg C. and the everolimus drug is stable up to 60 deg C. and is stable for short periods of time at temperatures between 60 and 80 deg C. Heating the PVDF-HFP coating with applied pressure will cause the PVDF-HFP coating to flow.

Additionally, as described above, the coating can be softened by a solvent in the coating. The solvent may be applied to the coating prior to radial compression or applied to the surface of the mandrel. A softened coating can also be provided by performing the coating operation in a manner that results in residual solvent in the coating after the coating step, for example, in the range of 1 to 10 wt % of the coating. Exemplary solvents for PVDF-HFP include acetone, dimethyl acetamide, dimethyl formamide, and dimethyl sulfoxide. Exemplary solvents that swell, but do not dissolve PVDF-HFP include tetrahydrofuran, 1,4-dioxane, and ethyl acetate.

In these embodiments of forming grooves in a coating on a metallic scaffold, the radial compression that molds the grooves on the coating will not deform or form grooves in the underlying metallic scaffold. Thus, the groove depth is limited to the thickness or approximately the thickness of coating. However, in a multi-layer coating, the compression can deform two or more of the layers. Therefore, the groove depth, for example, can be up to the thickness of a therapeutic layer or up to the thickness of the therapeutic layer and primer layer.

Additional embodiments of making a stent with a metallic scaffold and a polymer coating with grooves in a coating of the lumenal surface of the stent include forming grooves on the metallic scaffold prior to coating. In such embodiments, an uncoated metallic scaffold is placed over a mandrel with longitudinally aligned grooves. The stent is radially compressed over the surface of the mandrel to form grooves in the metallic lumenal surface of the metallic scaffold. A crimping device such as that described above may be used to apply the radial pressure.

The radial pressure applied and temperature of the mandrel or stent surface is significantly higher than for forming grooves in a polymer. The radial pressure may be 100 to 2000 psi, or more narrowly, 200 to 1000, 300 to 1000, 500 to 1000, or 400 to 800 psi. The temperature can be 800 to 1000 deg C., 200 to 500 deg C., 400 to 600 deg C., 400 to 1000 deg C., 500 to 1000 deg C., 600 to 1000 deg C., or 800 to 1000 deg C.

The mandrel is made of a material that has a strength and hardness higher than the metallic scaffold. An exemplary metal for a metallic scaffold is cobalt chromium. Suitable materials for a mandrel for forming grooves in such a scaffold may include tungsten carbide, titanium carbide, titanium nitride, aluminum nitride, and boron nitride. Grooves in these very hard mandrel materials may be formed by laser machining or ion beam milling.

After molding the grooves in the lumenal surface of the scaffold, the scaffold may then be coated. The coating parameters may be adjusted to preserve the grooves, as described above.

It was indicated above that a stent may be fabricated from a sheet of polymer by rolling and bonding the sheet to form the tube. The sheet or the rolled up sheet can be machined to form a stent pattern. In further embodiments, a polymer stent with grooves on a lumenal surface can be formed by molding grooves on a surface a polymer sheet, forming a stent pattern in the sheet, and rolling and bonding the sheet with the pattern to form a stent. Alternatively, the grooves can be molded into the sheet after the pattern is formed.

The grooves are formed on the sheet along a direction that is parallel to the intended cylindrical axis of the rolled up sheet. The sheet is rolled up about this axis with the surface with grooves being the lumenal or inner surface.

The grooves on the polymer sheet, with or without the pattern already formed, can be formed with a plate having a surface with grooves. The grooved surface is pressed against the polymer sheet. The plate may be softened by heating the plate and the temperature of the plate or polymer surface can have the temperature ranges described above. Alternatively, a solvent may be used to soften the polymer surface.

An exemplary stent design made from a rolled up sheet is described, for example, in US 2010/0244304 and US 2006/0136041. The stent design includes opposing circumferentially adjacent modules which have longitudinally adjacent slide-and-lock radial elements which permit one-way sliding of the radial elements from a collapsed diameter to an expanded or deployed diameter, but inhibit radial recoil from the expanded diameter. The slide-and-lock elements may flex or bend; however, unlike stents described above that are compressed and expanded through flexing or bending of elements, no substantial plastic deformation of the elements may be necessary during expansion of the stent from a collapsed diameter to an expanded diameter.

In addition to the polymers disclosed above, stents, such as those made from rolled up sheets can be made from tyrosine-derived polycarbonates. These degradable polymers are derived from the polymerization of desaminotyrosyl-tyrosine alkyl esters. Exemplary polymers include poly(DTE carbonate), poly(DTB carbonate), poly(DTH carbonate), poly(DTO carbonate), and poly(DTBzl carbonate), respectively, desamino-tyrosyltyrosine, referred to as "DT." The pendent group (R) of the polycarbonates can also be, for example, ethyl, butyl, hexyl, octyl, and benzyl esters.

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through molecular movement. Tg of a given polymer can be dependent on the heating rate and can be influenced by the thermal history of the polymer as well as its degree of crystallinity. Furthermore, the chemical structure of the polymer heavily influences the glass transition by affecting molecular mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent comprising:
   providing a stent including a bioresorbable polymer scaffold and a bioresorbable polymer coating over at least a portion of the scaffold;
   disposing the stent over a tubular mandrel such that a lumenal surface of the stent faces a surface of the mandrel, wherein the surface of the mandrel has a plurality of grooves aligned longitudinally; and
   radially compressing the stent over the surface of the mandrel such that the grooves at the surface of the mandrel form grooves on the lumenal surface of the stent, wherein the grooves on the luminal surface are aligned along a cylindrical axis of the stent further comprising disposing the stent over the mandrel into a sliding wedge crimper, wherein the crimper applies pressure to the stent to radially compress the stent over the surface of the mandrel.

2. The method of claim 1, wherein the grooves are formed in the coating polymer on the luminal surface.

3. The method of claim 1, wherein the luminal surface is free of coating polymer and the grooves are formed in the polymer of the scaffold.

4. The method of claim 1, wherein the mandrel comprises a heating element to heat the lumenal surface of the stent during the radial compression.

5. The method of claim 1, further comprising heating the lumenal surface of the stent during the radial compression to soften a polymer at the luminal surface to facilitate forming the grooves.

6. The method of claim 1, wherein a polymer on the lumenal surface of the stent is softened by a solvent during the radial compression to facilitate forming the grooves.

7. The method of claim 1, wherein a width of the grooves is 5 to 30 microns and a depth of the grooves is 0.5 to 20 microns.

8. A method of making a stent comprising:
   providing a stent having a metallic scaffold and a polymer coating over the scaffold;
   disposing the stent over a tubular mandrel such that a lumenal surface of the stent faces a surface of the mandrel, wherein the surface of the mandrel has a plurality of grooves aligned longitudinally; and
   radially compressing the stent over the surface of the mandrel such that the grooves at the surface of the mandrel form grooves on the coating over the lumenal surface of the stent further comprising disposing the stent over the mandrel.

9. The method of claim 8, further comprising heating the lumenal surface of the stent during the radial compression to soften the coating polymer to facilitate forming the grooves.

10. The method of claim 8, wherein the coating polymer on the lumenal surface of the stent is softened by a solvent during the radial compression to facilitate forming the grooves.

11. The method of claim 8, wherein a width of the grooves is 5 to 30 microns and a depth of the grooves is 0.5 to 20 microns.

12. A method of making a stent comprising:
   providing a stent having a metallic scaffold;
   disposing the stent over a tubular mandrel such that a lumenal surface of the scaffold faces a surface of the mandrel, wherein the surface of the mandrel has a plurality of grooves aligned longitudinally; and
   radially compressing the stent over the surface of the mandrel such that the grooves at the surface of the mandrel form grooves on the lumenal surface of the metal of the scaffold further comprising disposing the stent over the mandrel.

13. The method of claim 12, further comprising forming a coating comprising a polymer over at least the lumenal surface of the scaffolding, wherein the coated lumenal surface includes the grooves of the stent scaffold.

14. The method of claim 12, further comprising forming a coating comprising a polymer over at least the ablumenal surface of the scaffolding, wherein the lumenal surface with the grooves is free of a coating.

* * * * *